United States Patent [19]

McAndless

[11] Patent Number: 4,548,072

[45] Date of Patent: Oct. 22, 1985

[54] CONSTANT PRESSURE/G-FORCE DIFFUSION CELL SYSTEM

[75] Inventor: John M. McAndless, Medicine Hat, Canada

[73] Assignee: Her Majesty the Queen in right of Canada, as represented by the Minister of National Defence, Ottawa, Canada

[21] Appl. No.: 637,689

[22] Filed: Aug. 3, 1984

Related U.S. Application Data

[63] Continuation of Ser. No. 397,354, Jul. 12, 1982, abandoned.

[30] Foreign Application Priority Data

Sep. 4, 1981 [CA] Canada ................................. 385280

[51] Int. Cl.[4] ............................................. G01N 33/18
[52] U.S. Cl. ........................................ 73/159; 73/73
[58] Field of Search ................... 73/159, 73; 104/430, 104/409

[56] References Cited

U.S. PATENT DOCUMENTS

| | | | |
|---|---|---|---|
| 2,400,481 | 5/1946 | Brabender | 73/159 |
| 2,942,463 | 6/1960 | Mann | 73/159 |
| 3,886,057 | 5/1975 | Bredeweg | 73/73 |

OTHER PUBLICATIONS

Brochure; Honeywell; "Water Vapor" #52-5018, Apr. 4, 1966.

Primary Examiner—Charles Frankfort
Assistant Examiner—Denis E. Corr
Attorney, Agent, or Firm—Cushman, Darby & Cushman

[57] ABSTRACT

The invention disclosed is a device for monitoring the penetration of vapor from a challenge liquid occluded by a garment material, through the garment material, wherein pressure is applied against the garment material. The vapor which penetrates through the garment material is picked up by an inert carrier gas and detected to determine the protection afforded by the garment material against penetration by the challenge liquid/vapor.

8 Claims, 1 Drawing Figure

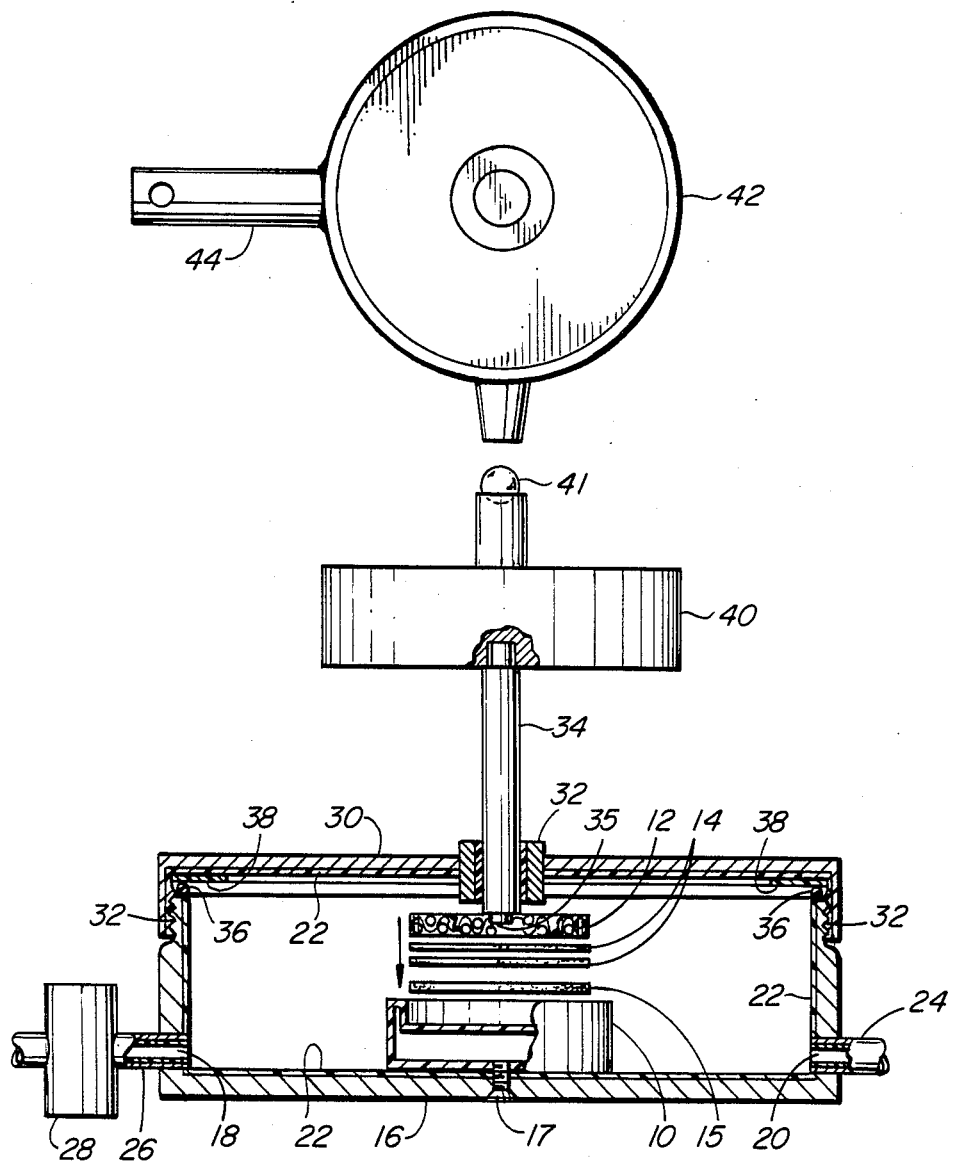

CONSTANT PRESSURE/G-FORCE DIFFUSION CELL SYSTEM

CROSS REFERENCE TO RELATED APPLICATIONS

This application is a continuation of our earlier application Ser. No. 397,354 filed July 12, 1982, now abandoned.

This invention relates to the protection afforded by protective garments against liquid/vapour penetration, and in particular to an apparatus for the assessment of the protective capability of such garment materials when challenged by occluded liquid, under pressure. An example of the problem is that of aircrew sitting on liquid contamination during the course of a mission where aircraft maneuvering during a mission may produce high transient G-forces. With transient G-forced excluded, a situation where an individual e.g. a vehicle driver, wearing protective clothing exerts a constant pressure against liquid contamination for a prolonged period of time, is simulated.

Garments are presently assessed for their protective capabilities in terms of the amount of vapour which has penetrated after a given length of time e.g. 24 hours or the time before vapour first penetrates after the garment is challenged.

The penetration of vapour through protective ensembles is normally measured using a diffusion cell or penetration cell which contains fabric sample(s) located at the interface of two chambers. The top chamber may be open to the air, closed or flushed with a gas, usually air. The bottom chamber is usually slowly flushed with air or inert gas that has been passed through an absorbent filter to remove any trace contaminants. Penetration tests can be performed in two different ways:

1. known concentrations of challenge vapour in a carrier gas may be directed at the upper fabric surface, or
2. liquid drops may be statically emplaced (drop touch-off method) or impacted upon the upper fabric surface.

In both cases, any vapour penetrating the fabric sample can be collected from the lower chamber in bubblers for subsequent analysis or monitored continuously using such devices as ionization or hydrogen flame emission detectors.

To simulate the effect of pressure, weighted plates or plunger assemblies may be used to press drops which have come in contact with the upper fabric surface. Penetration of vapour and liquid can be detected by means of the colour development of specially-treated paper in contact with the underside of the fabric or by means of bubblers or real-time monitors.

The usual penetration or diffusion cell test does not simulate the case where an individual wearing protective clothing exerts a constant pressure against liquid contamination; for example, by sitting on liquid drops, leaning against a wetted surface or carrying equipment such as a backpack which is pressing against the surface of the clothing where liquid drops reside.

In the case of high performance aircraft where the cockpit has received liquid contamination, especially on the seat cushion, the pilot sitting on the liquid exerts a continual constant pressure throughout his flight mission. In addition, he may be subjected to high, transient G-forces due to aircraft maneuvering. The standard diffusion cell system is unable to simulate these aircraft related conditions of constant pressure and/or transient G-forces as applied to liquid occluded by a protective garment.

The use of weights or plunger assemblies applied to liquid drops on the upper surface of a fabric can provide the necessary pressure. However, some of the limitations to using these methods are listed below:

1. The weights or plungers are usually made of non-absorbing materials such as metal or plastic. That is, their effect is not that of an absorbing substrate such as a seat cushion which has been wetted by the challenge liquid and then occluded (covered) by the protective ensemble. The use of absorbing material (e.g. fabric) on the contact faces of the weights or plunger assemblies can correct this problem;
2. Normally the fabrics in a diffusion cell are supported at the edges only. Therefore, only small amounts of pressure can be applied to the fabric by weights without causing weave distortion, leakage at the edges or eventually loss of grip by the test cell on the sample;
3. The orientation of the pressure-applying weights, liquid challenge and fabrics is not the same as the real situation. That is, in the case of an individual sitting on liquid contamination, the liquid is occluded by the garment, (not the weight) and the pressure is applied through the garment itself to a solid substrate (not through the liquid drops directly to an edge-supported substrate). This latter point may be important in terms of the fabric structural distortion caused by the applied pressure and how this structural distortion effects vapour penetration.

According to one embodiment of the invention, an apparatus for monitoring the penetration of occluded fluid through a garment material subjected to pressure applied against the garment is contemplated, comprising: sample cup means for supporting a sample of said garment material; pressure plate means of a suitable porous material, operable in said sample cup means for applying pressure to said garment material; and detector means for monitoring the penetration of vapour from a liquid initially occluded by said garment material, through said garment material and said pressure plate means.

In the drawing which illustrates the preferred embodiment of the invention, the FIGURE is a side elevation in section of the apparatus according to the invention.

Referring to the drawing, the novel apparatus comprises a cylindrical sample cup means 10 for disposition of pressure plate means 12. Pressure plate means 12 is made of a suitable porous material and is operable in sample cup means 10 for applying pressure to a garment material (or materials) 14 which is fully supported in said sample cup means. Detector means (not shown) is disposed to monitor the penetration of vapour from a liquid initially occluded by said garment, through said garment material and said pressure plate means.

More specifically, sample cup means 10 is centrally located in the bottom of air-tight chamber means 16 and conveniently retained by a self-tapping screw 17. Inlet means 18 is provided in chamber means 16 for introducing an inert carrier gas e.g. air and nitrogen. Outlet means 20 is provided in chamber means 16 for removal of the carrier gas. Detector means (not shown) is connected to outlet means 20 for monitoring the penetration of a vapour from a liquid initially occluded by the garment material 14 and carried by said carrier gas to said detector means. Thus a challenge liquid is placed in the bottom of the sample holder 10, conveniently on an absorbing or non-absorbing substrate 15. The substrate simulates, for example, a seat cushion. A sample of the garment material of slightly smaller diameter than that of the sample holder is placed over the substrate 15 and pressure is applied to the other side of the garment material 14 by pressure plate means 12. Any challenge vapours permeating the garment material and the porous plate will be picked up by the carrier gas and flow out of the air-tight chamber 16 through outlet means 20 which is connected to the detector (not shown). The detector is conveniently a photoionization detector and recorder system for providing real-time vapour concentration monitoring and a flow meter.

All parts of the apparatus downstream of the inlet means which are in contact with the carrier gas including sample holder 10 pressure plate means 12 and the inside of the air-tight chamber 16, are coated with a suitable inert plastics material liner 22 such as polytetrafluoroethylene (Teflon ®) to prevent vapour adsorption. Outlet conduit 24 also includes a Teflon liner.

Inlet conduit 26 includes filter means 28 to remove trace contaminents from the carrier gas. A charcoal-containing canister has been successfully employed.

Screw-threaded closure means 30 is provided to close the top of the air-tight chamber 16, including threads 32 which engage complementary threads on the chamber 16. A rubber O-ring 36 and flat Teflon slip ring 38 are provided to ensure air-tight engagement. Closure means 30 includes a central opening fitted with an air-tight Teflon-lined gland 32 to provide movable access for push rod 34 to the chamber 16. Thus, push rod 34 is free to move vertically to impart corresponding movement of pressure plate 12 in sample holder 10, while maintaining an air-tight seal.

Push rod 34 is made of fluorochemical-treated stainless steel. Pressure plate 12 is one square inch in area and is conveniently made of fluorochemical-treated stainless steel expanded mesh with metal supports containing large openings. Alternatively, both the push rod and the pressure plate can be made of Teflon or coated with Teflon to minimize adsorption effects. The push rod 34 includes an extension 35 which seats in the central opening of pressure plate 12.

Means for controlling the pressure applied by pressure plate means 12 to garment material 14 is also provided. To apply a constant pressure, a weight 40 is attached to the extension of push rod 34 outside the chamber 16. Transient pressure loads are applied to the push rod 34 and ultimately pressure plate means 12 by additional weight 42 carried by a pivoting lever arm 44. Lever arm 44 rests on and is acted upon by a conventional cam means (not shown) to impart an extra, transient pressure load on the weighted free end of push rod 34. As the cam rotates, weight 42 periodically contacts a fixed ball 41 which ensures even distribution of the additonal weight down through push rod 34. The cam means is driven by a conventional 1 r.p.m. electric motor.

In operation fabric sample circles cut to slightly larger than one square inch area may be inserted into the sample cup 10 (which may or may not contain an absorbing substrate 15, such as another fabric) and placed directly over a drop (or drops) of challenge liquid which have been delivered by means of a syringe. The porous pressure plate 12 is placed on top of the fabric samples 14, the push rod 34 inserted through the gland opening 32 and the closure 30 tightened down on the chamber 16 so that an airtight seal is formed. Care is taken to ensure that the push rod fits snugly to the centre cavity of the pressure plate before closing the chamber. An appropriate weight 40 (e.g. 2 lbs) is mounted on the push rod 34 extending through the gland 32. Once assembled, this set up provides a constant pressure to the fabric ensemble and occluded liquid (e.g. 2 lbs in $^{-2}$). Transient G-forces (transient extra pressure) are applied to the ensemble under test by means of extra weights 42 affixed to lever 44 and driven by a conventional cam means (not shown).

When properly positioned, rotation of the cam causes the lever to lower suddenly, the extra weight to contact the weight attached to the exterior end of the push rod and hang free of the cam, adding extra weight and thus extra pressure to the ensemble in the sample cup. Further rotation of the cam raises the lever from the weighted push rod, thereby restoring the initial constant pressure. The cam is two-sided, lowering and raising the lever twice for 15 seconds duration in each case if allowed to turn continuously. (i.e. two (2) extra-pressure (G-force) applications per minute). The rate at which extra pressure is applied can be selected by turning the motor drive off and on at appropriate lever positions (raised or lowered) to the maximum of two applications per minute.

A flow meter can be used to check on the seal provided by the push rod gland and chamber closure or it may be placed before the canister to regulate carrier gas flow. Inert carrier gas (e.g. nitrogen) or air from a compressed cylinder is directed at a low flow rate (e.g. 20 mL min$^{-1}$) through the filter, chamber and detector. Vapour evolving through the fabric ensemble and porous pressure plate is carried from the chamber to the detector where a signal response is recorded. Generally, at the example flow rate, the time required for vapour to reach the detector from the sample is less than one minute, short time compared to the several hours normally required for vapour to penetrate the protective clothing ensembles tested.

Provided relatively low flow rates can be utilized, other types of detectors such as flame ionization detectors or solvent entrapment using bubblers could be used to detect the presence of evolving vapour in the diffusion cell. The photoionization detector is the preferred type for most applications as it requires no external fuel supply, is sensitive to most of the compounds of interest, is rugged, and can provide a means of drawing carrier gas through the diffusion cell using an integral fan if so required. In addition, this type of detector provides real-time monitoring of the vapour concentration in the cell. Thus, a change in detector response from baseline conditions can be related to the time at which vapour first penetrates the ensemble under test. In addition, by recording vapour concentration with time and integrating the response curve so produced, the accumulated vapour dose at any given time can be calculated.

The embodiments of the invention in which an exclusive property or privalege is claimed are defined as follows:

1. An apparatus for monitoring the penetration of vapour from an occluded liquid through a garment material subjected to pressure applied against the garment, comprising:
    sample cup means for supporting the entire surface of a stationary sample of said garment material and including means for carrying a liquid pressure plate means of a suitable porous material, operable in said sample cup means for applying pressure to the entire surface of said sample of garment material;

means for applying a pressure load to said pressure plate means; and detector means for monitoring the penetration of vapor from said liquid initially occluded by said garment material, sequentially through said garment material and then said pressure plate means.

2. An apparatus according to claim 1, wherein said pressure load is a constant pressure load.

3. An apparatus according to claim 1, wherein said pressure load is a transient pressure load.

4. An apparatus for monitoring the penetration of vapour from an occluded liquid through a garment material subjected to pressure applied against the garment, comprising air-tight chamber means;

inlet means in said chamber means for introducing an inert carrier gas into said chamber means;

outlet means in said chamber means;

sample cup means for supporting a sample of said garment material over substantially its entire surface and including means for carrying a liquid;

pressure plate means of a suitable porous material disposed in said chamber means, for applying pressure to the entire surface of said sample of garment material fully supported in said sample cup means;

means for applying a pressure load to said pressure plate means; and detector means connected to said outlet means for monitoring the penetration of vapor from said liquid initially occluded by said garment material, sequentially through said garment material and then said pressure plate.

5. An apparatus according to claim 4, wherein said pressure load is a constant pressure load.

6. An apparatus according to claim 4, wherein said pressure load is a transient pressure load.

7. An apparatus according to claim 5 or 6, wherein said means carrying said liquid is a substrate material covered by said garment material.

8. An apparatus according to claim 4, 5 or 6, wherein the air-tight chamber means, pressure plate means, pressure load applying means and outlet means are coated with inert plastics material.

9. An apparatus according to claim 1, including means for applying a pressure load to said pressure plate means.

* * * * *